(12) United States Patent
Imazu et al.

(10) Patent No.: US 6,171,280 B1
(45) Date of Patent: Jan. 9, 2001

(54) ASPIRATOR HAVING DUAL INTER-OPERATING MANIPULATION UNITS

(75) Inventors: Masanori Imazu, Takasago; Yoshiyuki Tsuru, Kobe; Tadashi Bandou; Kazuya Fukuda, both of Kakogawa, all of (JP)

(73) Assignee: Sysmex Corporation, Kobe (JP)

( * ) Notice: Under 35 U.S.C. 154(b), the term of this patent shall be extended for 0 days.

(21) Appl. No.: 09/385,853

(22) Filed: Aug. 30, 1999

(30) Foreign Application Priority Data

| Aug. 31, 1998 | (JP) | 10-244486 |
| Aug. 31, 1998 | (JP) | 10-244521 |
| Sep. 14, 1998 | (JP) | 10-259647 |

(51) Int. Cl.$^7$ .................................................. A61M 1/00
(52) U.S. Cl. ........................... 604/118; 604/119; 604/128
(58) Field of Search ................................. 604/118, 119, 604/128, 139, 148, 317

(56) References Cited

U.S. PATENT DOCUMENTS

| 4,180,074 | * | 12/1979 | Murry et al. | 604/31 |
| 4,713,052 | * | 12/1987 | Beck et al. | 604/48 |
| 5,201,232 | | 4/1993 | Uffenheimer . | |
| 5,364,342 | * | 11/1994 | Beuchat et al. | 604/30 |
| 5,387,204 | * | 2/1995 | Olsson et al. | 604/317 |
| 5,403,276 | * | 4/1995 | Schechter et al. | 604/22 |
| 5,662,611 | * | 9/1997 | Beiser et al. | 604/118 |
| 5,700,240 | * | 12/1997 | Barwick, Jr. et al. | 604/22 |
| 5,720,721 | * | 2/1998 | Dumas et al. | 604/67 |

FOREIGN PATENT DOCUMENTS

| 0 795 742 A1 | 9/1997 | (EP) . |
| 2511549 | 4/1996 | (JP) . |
| 9-304400 | 11/1997 | (JP) . |

* cited by examiner

Primary Examiner—Sharon Kennedy
Assistant Examiner—Kevin C. Sirmons
(74) Attorney, Agent, or Firm—Shinjyu Intellectual Property Firm

(57) ABSTRACT

First and second aspirator manipulation units operate a single-pipette in a coagulation analyzer for aspirating plasma samples from both rubber-capped as well as uncapped vessels. A first holder in the first aspirator manipulation unit actually retains the pipette, while a second holder in the second aspirator manipulation unit is configured to enclose the first holder leaving a predetermined amount of play. To move the pipette toward a sample vessel in a rack that has been shifted into aspiration position, the holders in the manipulation units are inter-fitted, and are translated down. If the pipette strikes a cap, a sensing means in the first aspirator manipulation unit signals a controller to operate the first aspirator manipulation unit to back the pipette upward slightly. Thereupon, the controller, via the second aspirator manipulation unit, actuates the second holder alone to press on the first holder to stab the pipette through the cap. For this operation, the pipette tip is cut obliquely and the rim of its inner wall is specially chamfered to prevent the punctured rubber in the cap from clogging the tip. After the pipette aspirates an aliquot of the plasma sample, the controller actuates the second holder in reverse to draw the pipette out from the cap. The first aspirator manipulation unit carries out other pipette manipulation operations alone. Accordingly, the pipette is driven differentially in accordance with the capped/uncapped status of the vessel present in the aspiration position.

12 Claims, 8 Drawing Sheets

ASPIRATOR HAVING DUAL INTER-OPERATING MANIPULATION UNITS

BACKGROUND OF THE INVENTION

1. Technical Field

The present invention relates to precision aspirators, suited for use in automated liquid sample analyzers, for taking up liquid from containers by suction. In particular the invention relates to precision aspirators employing liquid suction tubes that can pierce caps sealing the mouths of containers holding diagnostic samples and reagents, and that can discriminate among such containers.

2. Description of Related Art

Automated liquid sample analyzers, for example, blood-sample analyzing machines, employ an aspirating pipette to take up a predetermined amount, or aliquot, of sample liquid such as blood plasma sequentially from a row of tubular sample containers. The sample containers are held in a sample rack that is transferred in container-by-container increments into an aspirating position beneath the pipette. Each container is paused in the aspirating position, in which a mechanism manipulating the pipette brings it down into the container, actuates suction through the pipette to take up an aliquot, brings the pipette back up, and shifts it to an ejecting position. In the ejecting position, the aliquot is ejected into, for example, a reaction vessel containing reagents for a blood-analyzing test.

Some of the containers loaded into the sample rack may be sealed, with a rubber cap for example, or otherwise stoppered. The tips of the needle-type aspirating pipettes used for taking up aliquots from sample containers are cut obliquely to pierce a sealed or stoppered container.

An aspirating tube having an aspiration aperture formed on its circumferential surface apart from the tip, so that when the aspirating tube penetrates a rubber cap, rubber debris does not clog the aspirating tube, as Japanese Laid-Open Pat. App. No. 9-304400 discloses, is known.

On the other hand, Japanese Pat. No. 2511549, corresponding to U.S. Pat. No. 5,201,232, discloses a liquid sampling device having a sampling probe for withdrawing sample liquids from open containers, as well as a sampling needle for closed containers. Therefore, the liquid sampling device is operable to suit either type of containers—capped (closed) containers, or uncapped (open) containers. Furthermore, the disclosed liquid sampling device distinguishes open containers from closed containers using a detector that reads an identification label or card provided on the container exterior.

Nevertheless, the device as taught in Japanese Pat. No. 2511549, in order to identify the containers from which it withdraws samples, requires special labels or cards affixed to the containers, as well as a detector to read them. Consequently, if the labels or cards are affixed improperly, the device cannot identify containers correctly. In addition, equipping the device with two kinds of aspirators makes the mechanism large and complex.

If for example a single aspirating tube is to be used for both open and closed containers, some situations make it desirable to provide the aspiration aperture in the tip of the aspirating tube. For instance, the desire to improve quantitating accuracy in micro-samples of a few $\mu l$, to decrease sample-liquid dead volume (the quantity that cannot be aspirated and remains in the container), or to decrease the amount of aspirating tube immersed into a sample liquid in order to prevent inter-contamination of the liquids necessitates that the aspiration aperture be in the tip of the aspirating tube. However, if the aspiration aperture is provided in the tip of the aspirating tube, the tube is likely to get clogged when it penetrates the cap of a closed container.

In conventional liquid sampling devices, the aspirating tube is shifted vertically to take up an aliquot, which operation requires relatively little force to bring the pipette down into an open container, yet considerably greater force to stab the pipette through a sealed container. Supplying large force for an open container leads to mechanical losses, hampers agility and, leads to operational problems such as damage to the aspirating tube by its being crushed on the bottom of the container due to the container's vertical position. For example, to shift horizontally the liquid aspirating tube and its large drive source if integrated into one unit confronts the practical problems that the unit cannot travel horizontally at high speed due to its large size and weight, and that the horizontal shifting mechanism then also must be large.

SUMMARY OF THE INVENTION

One object of the present invention is to enable correct identification of liquid sample containers by employing a container-identifying device of simple constitution.

Another object of the present invention is to prevent the aspiration aperture in the sharp tip of an aspirating pipette from becoming clogged.

A further object of the present invention is to enable manipulation of a sample-liquid aspirating pipette for both closed and open containers by accordingly supplying appropriate force, in an aspirator adapted for operation in, for example, an automated analyzer.

An aspirator in accordance with the present invention functions in an automated analyzer to aspirate liquid aliquots from a row of capped and uncapped containers in a sample rack. horizontally transferred by a sampler incrementally into an aspiration position. Essential components of the aspirator include a needle pipette having an obliquely cut aspiration tip, first and second aspirator manipulation units, external force sensing means associated with the first aspirator manipulation unit for detecting external force acting on the pipette, and liquid-surface detecting means operative through the pipette.

The first aspirator manipulation unit includes a first holder that retains the pipette vertically, and a first drive means that vertically translates the first holder into and out of a container in the aspiration position. The second aspirator manipulation unit includes a second holder configured to enclose the first holder, leaving a predetermined amount of play. A second drive means for the second aspirator manipulation unit cooperates with the first drive means to translate the second holder vertically in tandem with the first holder, and operates independently of the first drive means to drive the second holder against the first holder.

An aspirator controller is connected to the first and second drive means and is responsive to both the external force sensing means and the liquid-surface detecting means; accordingly the aspirator controls the first and second aspirator manipulation units.

The aspirator controller is programmed to actuate the first and second drive means to translate the first and second holders vertically in tandem. If no external force is detected acting on the pipette by the external force sensing means, the controller continues to direct the first and second drive means to bring the pipette down until it contacts liquid in a container in the aspiration position. If the needle pipette does not contact liquid in the container in the aspiration position after the first and second holders have been translated a predetermined distance, the controller halts the first and second drive means. If external force is detected acting on the pipette by the external force sensing means, i.e., if the pipette tip strikes the top of a capped or stoppered container, the controller halts the first drive means and continues actuating the second drive means. This operation presses the second holder onto the first holder to stab the pipette through the cap or stopper.

Therein, to prevent the punctured rubber in the cap from clogging the tip, the obliquely cut aspiration tip of said needle pipette is inner-rim chamfered.

The aspirator operates automatically and checks for the presence of a cap/stopper on each container. Accordingly, in translating the first and second holders downward to the container, if the pipette does not encounter a cap/stopper, the second holder remains separated from the first holder within the predetermined amount of play. Consequently, the first holder, retaining the pipette, is shifted solely by the force from the first drive source.

On the other hand, if the container currently in the aspiration position is closed, the second holder alone is driven, and presses down on the first holder. Consequently, the stabbing pipette is actuated solely by the force from the second drive source.

Accordingly, the first drive source supplies relatively small force to the pipette in translating it vertically, whereas the second drive source supplies relatively large force to the pipette to stab it vertically through a cap/stopper. That is, the drive mode (the magnitude of force supplied) for shifting the pipette is altered accordingly, eliminating mechanical losses occurring otherwise, and gaining agility and reliability in the operation of the aspirator.

The aspirator in accordance with the present invention employs the pipette to discriminate closed from open containers, wherein the fact that a present container is either open or capped/stoppered is identified. Furthermore, since the aspirator can determine absence of liquid contact and of external force acting on the pipette after translating the pipette a predetermined distance, the aspirator therefore can determine that there is no liquid present or that there is no container present. The drive sources in this case can be controlled accordingly not to lower the pipette any further, preventing it from damage.

In accordance with the present invention, as described above, since the presence of a cap/stopper is directly detected using the pipette, misjudgment in identifying containers is unlikely.

The pipette employed in an aspirator embodied in accordance with the present invention is preferably made of metal for strength, and because the aspirator's liquid-surface detection capability derives from capacitance established in the pipette. Further, to impart anticorrosion and anti-abrasion properties to the pipette, it is preferable that it is manufactured from stainless steel tubing whose outer surface is coated with a hard coating such as chromium nitride (CrN).

As noted above, to prevent clogging at the tip of the pipette, the obliquely cut surface is preferably inner-rim chamfered; i.e., formed not to give rise to acute-angle edges on the inner circumferential rim of the tip opening The entire inner circumferential rim of the obliquely cut pipette tip opening may be chamfered to remove any and all acute-angle edges present on the rim. However, only that half of the inner circumferential rim where acute-angle edges arise when the pipette tip is cut may alone be chamfered.

Types of liquid that may be aspirated by the pipette are not particularly limited; one example wherein the aspirator is employed in an automated analyzer, however, is blood samples such as plasma. In automated analyzers, containers holding the liquid samples for assaying are preferably loaded into a sample rack that is conveyed into aspirating position beneath the pipette. More specifically, in automated analyzers a device known as a sampler functions to transfer the sample rack, into which a plurality of containers are set or "loaded," sequentially into position beneath the pipette for aspirating aliquots from the containers vessel-by-vessel.

Concerning use of the aspirator, it is preferable that the first aspirator manipulation unit including the external force detection means is horizontally shiftable.

From the foregoing explanation, it will be understood that though the surface of the liquid contained differs in position with each open container, in response to the liquid-surface detection means the controller halts the first drive source to stop the downward travel of the pipette. In particular, the amount of liquid that attaches unnecessarily to the aspirating tube may be minimized. In addition, though the position of the bottom of each open container may differ, in response to the external force detection means the controller halts the first drive source to stop the downward travel of the pipette. This prevents the pipette from crashing and breaking on the bottom of the container.

With closed containers, after the pipette has been stabbed through a cap/stopper, in response to the liquid-surface detection means the controller halts the second drive source to stop the downward travel of the pipette.

It is preferable that the external force detection means includes a sensor that detects colliding of the pipette tip against an obstacle. This type of sensor is usually known as a "crash sensor" and is provided for detecting crashing of the pipette against an object. The pipette is stopped immediately after it hits an object and is evacuated in order to avoid damaging itself. In accordance with the present invention, then, the containers employed in an automated analyzer into which the aspirator as described above is adapted may be identified using such a crash sensor provided in the aspirator.

The foregoing and other objects, features, aspects and advantages of the present invention will become more apparent from the following detailed description in conjunction with the accompanying drawings.

DETAILED DESCRIPTION OF THE PREFERRED EMBODIMENTS

Figure 2:
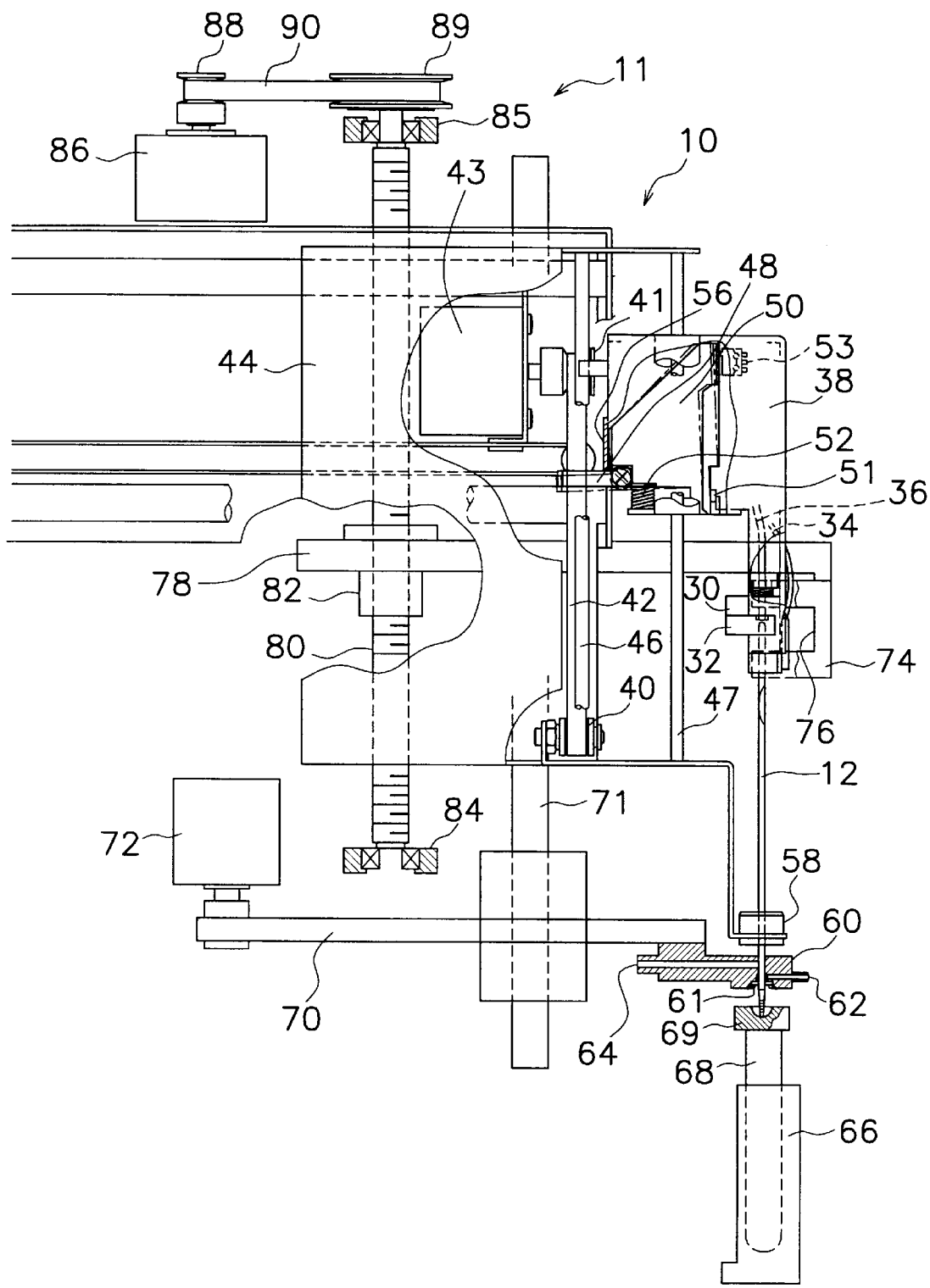
FIG. 2 is a partially cut away, partly in section, fragmentary view corresponding to FIG. 1, illustrating details of the aspirator mechanism.

The aspirator in this embodiment is built into a blood coagulation analyzer. FIG. 2 is an end view seen from the left side of the blood coagulation analyzer with respect to an operator, wherein the right side of the figure is the front end of the device and the left side is the device interior. A sample rack 66 that holds a plurality of sample containers 68 lined in a row is transferred one container at a time by a sampler (not shown) in the direction in the figure from the reverse to the obverse face of the sheet.

Figure 1:
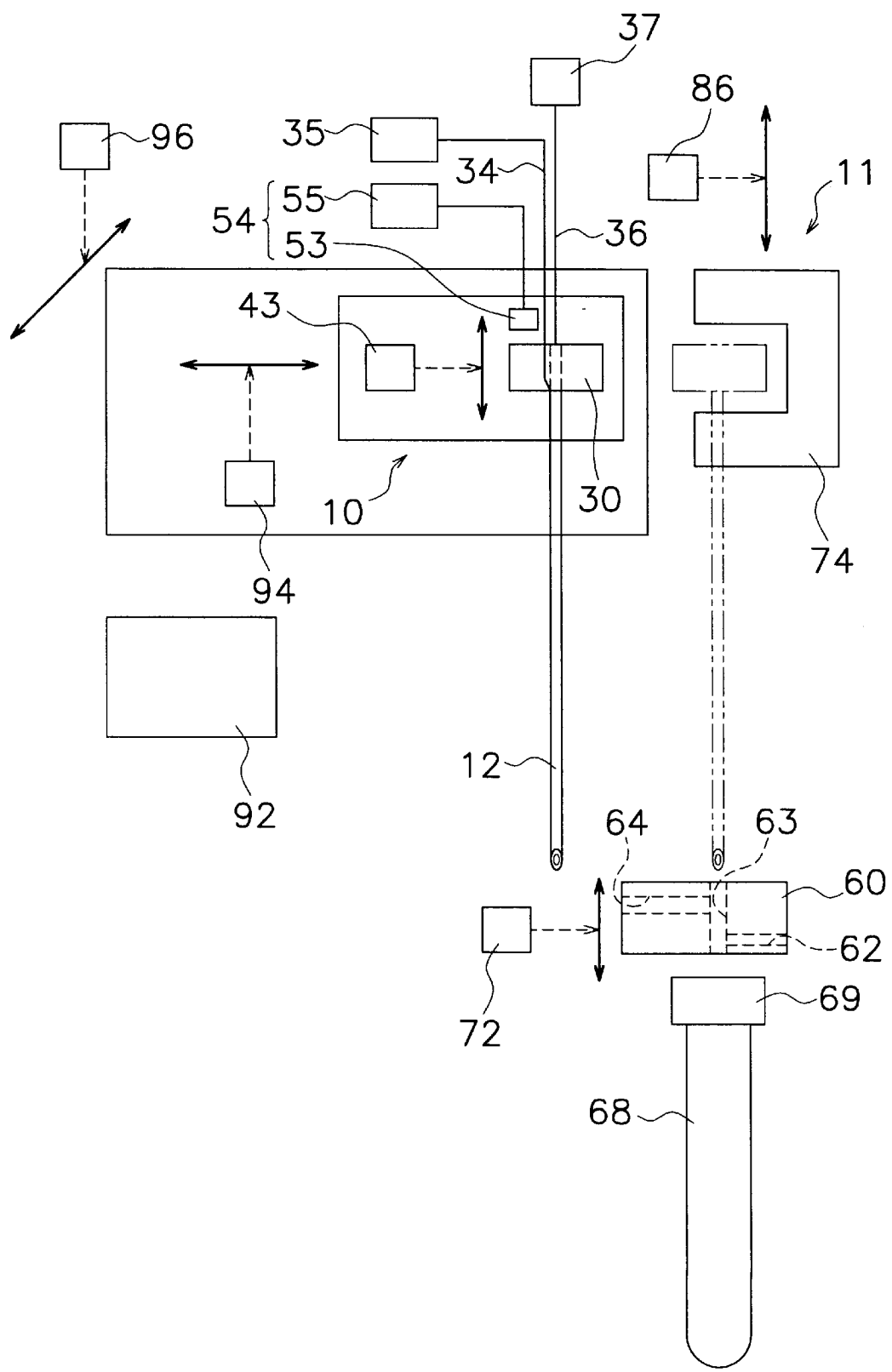
FIG. 1 is a schematic rendering of the general configuration of an aspirator in accordance with the present invention, seen from the left side of the device with respect to an operator.

As shown in FIG. 1, the aspirator comprises a first aspirator manipulation unit 10 and a second aspirator manipulation unit 11. The first aspirator manipulation unit 10 is provided with a first holder 30 that holds a pipette 12, which is a liquid aspirating pipe, and a first drive source 43 that shifts the first holder 30 up and down. The second aspirator manipulation unit 11 is provided with a second holder 74 that engages the first holder 30, and a second drive source 86 that shifts the second holder 74 up and down. The first aspirator manipulation unit 10 is made to be horizontally shiftable. The double-dotted broken lines in FIG. 1 indicate the situation in which the first aspirator manipulation unit 10 is in its forward-most position, and the first holder 30 is adjacent the second holder 74 where the two can engage. The solid lines indicate the situation in which the first aspirator manipulation unit 10 is in its rearward position, and the first holder 30 is apart from the second holder 74 where the two cannot engage.

The pipette 12 has an inner passage 14 (referring to FIG. 4), and is a cylindrical pipe made of stainless steel having an outer diameter of 2.0 mm, an inner diameter of 1.3 mm and overall length of 130 mm. An electric wire 34 is attached to the upper end portion of the pipette 12. The electric wire 34 is connected to a liquid-surface detection circuit 35, which detects liquid surfaces based on the change in capacitance when the tip of the pipette 12 contacts the surface of a liquid. A tube 36 is joined to the top end of the pipette 12, and connected to a liquid quantity meter 37 such as a syringe pump. In this embodiment, the first aspirator manipulation unit 10 is shifted horizontally by respective third and fourth drive sources 94, 96.

Figure 3:
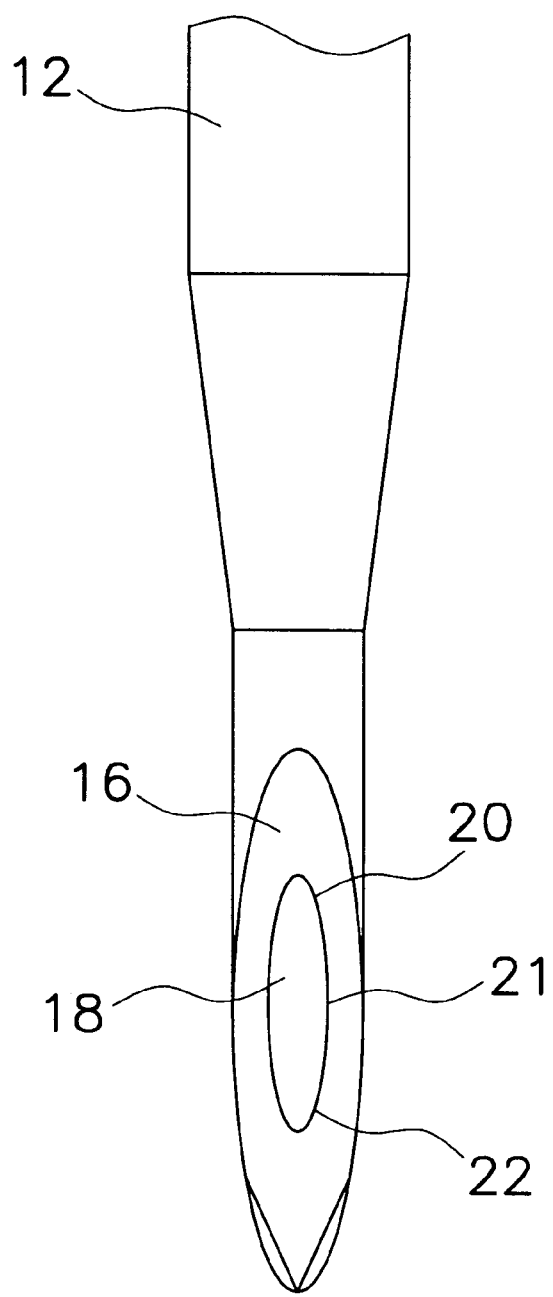
FIG. 3 is a fragmentary, enlarged view depicting the tip of a pipette employed in the aspirator.
Figure 4:
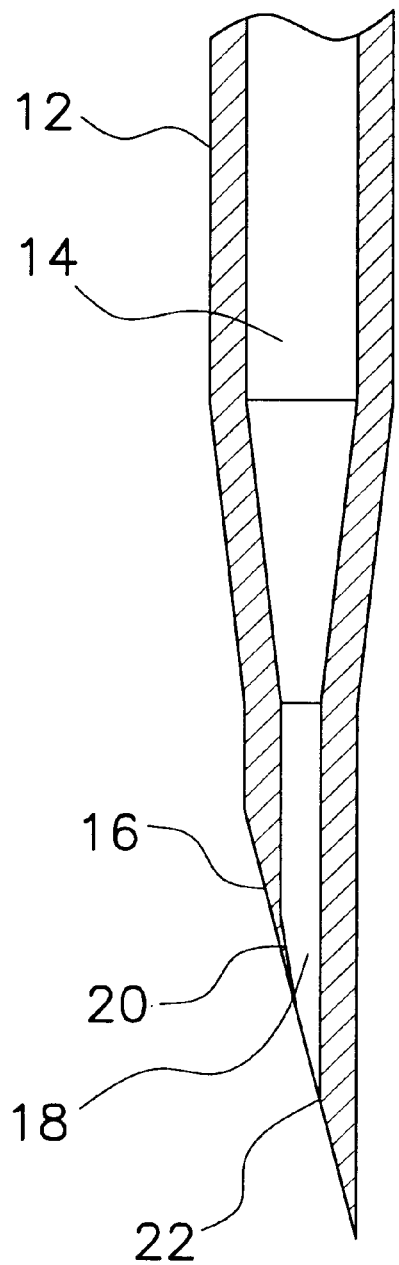
FIG. 4 is a transverse sectional view corresponding to FIG. 3.

Referring to FIGS. 3 and 4, the pipette 12 near the lower end is constricted, narrowing to 1.2 mm outer diameter and 0.5 mm inner diameter, and as shown in the figures is sharply cut obliquely with respect to the pipette axis. The inner passage 14 opens in aperture 18 on oblique-cut surface 16. Merely by being cut just obliquely, an acute-angle edge arises on the inner wall rim 21 of the oblique-cut surface 16 (the acute-angle edge arises around the upper half 20, and an obtuse angle edge arises around the lower half 22.)

Figure 5:
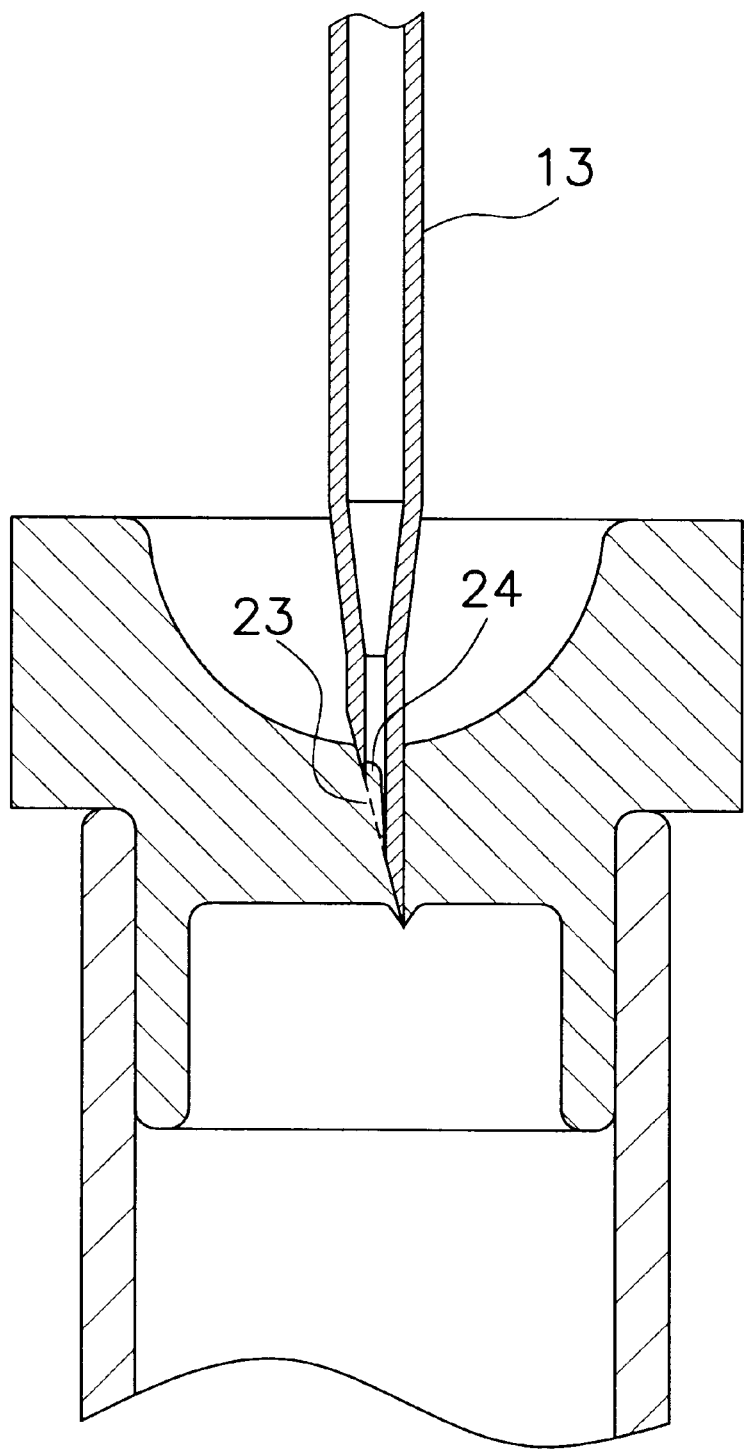
FIG. 5 is a fragmentary, enlarged sectional view illustrating the tip of a conventional pipette penetrating a stoppered sample vessel.

FIG. 5 shows the situation wherein a conventional pipette 13 stabs a rubber cap. An acute-angle edge 23 present on the inner wall rim severs the rubber cap 24 when the pipette 13 stabs it, and a portion of the severed rubber cap (a rubber crumb) gets into the opening such that it is immediately blocked.

Therein, a chamfering process for removing the acute-angle edge is carried out on the upper circular half 20 of the oblique-cut surface 16 on the constricted lower end of the pipette 12. This accordingly does away with the acute-angle edge around the entire inner wall rim. Even in continuous tests of at least 30,000 times it was confirmed that no blockage occurred in the piercing end of a pipette thus configured.

A region of the outer wall of the pipette 12, about 80 mm from the bottom, is subjected to a chromium nitride (CrN) coating process in order to elevate its anti-abrasion properties.

Turning again to the end view in FIG. 2 of an embodiment of an aspirator, a first chassis 44 serves as a framework for the first aspirator manipulation unit 10. A belt 42 connects pulleys 40 and 41, and pulley 41 is directly connected to the shaft of the first drive source 43 (a stepping motor in this embodiment). A rocker piece 50 is pivotably supported on a second chassis 38 and is attached to a portion of the belt 42 via a clasp 48. The second chassis 38 is guided by vertically restricting guide shafts 46 and 47 that are mounted on the first chassis 44. The first holder 30, in which the pipette 12 is retained, is also mounted on the second chassis 38. Accordingly, by actuating the first drive source (stepping motor) 43 to turn the pulley 41, the rocker piece 50 can be shifted up and down in attachment to the belt 42, wherein the first holder 30, the second chassis 38, and the rocker piece 50 are shifted together vertically.

An urging means 52, in this case a coiled compression spring, is disposed between the second chassis 38 and the rocker piece 50. In the state wherein no external force is acting on the pipette 12, the rocker piece 50 is urged clockwise in FIG. 2 on a fulcrum 51, and contacts an abutment 56 provided on the second chassis 38.

An external force detection means 54 for detecting upward external force when acting on the pipette 12 is provided in the first aspirator manipulation unit 10, as indicated in FIG. 1. The external force detection means 54 comprises a sensor 53, in this case a micro-switch, and an external force detection circuit 55 to which the sensor 53 is electrically connected.

If when descending the pipette 12 comes into contact with something such that an external force acts upwardly on it, the fulcrum 51 side of the second chassis 38 halts, but the clasp 48 side of the rocker piece 50 shifts downwardly. The rocker piece 50 is therefore rotated relatively counterclockwise as indicated by the double dotted broken lines in FIG. 2, against the compressive force of the spring 52. The micro-switch 53 senses this very slight fluctuation, which is detected by the external force detection circuit 55 through its electrical connection to the micro-switch 53.

A guide grommet 58, attached to the first chassis 44, functions as a guiding means for the vertically travelling pipette 12. Because the pipette 12 is 100 mm or longer, the guide grommet 58 is furnished in this embodiment so that the pipette 12 will not quiver horizontally when it is travelling.

A washing element 60 having a through-hole 63 (shown in FIG. 1) cleanses the wall of the pipette 12 by supplying cleansing fluid from a port 62 to the through-hole 63, and discharging waste fluid from a port 64. The washing element 60 is shifted up and down by a drive source 72, in this case an air cylinder, via a link 70 guided on vertically disposed guide rail 71.

Whereas the first aspirator manipulation unit 10 has just been described, the second aspirator manipulation unit 11 will in turn be explained. The second holder 74 is engageable with the first holder 30. The blood coagulation analyzer is configured in this embodiment such that two holders 30 and 74 couple by convex-concave intermeshing. Specifically, the first holder 30 includes convex part 32. The second holder 74 has a concave part 76 into which the convex part 32 fits with a gap. The vertical width of the convex part 32 is about 6 mm, and that of the concave portion 76, 14 mm. Accordingly, the first holder 30 has room to travel without interference from the second holder 74, i.e., it has non-interference margin of 8 mm.

The second holder 74 is shifted up and down by a mechanism as follows. A drive shaft 80 having a spiral groove is rotatably supported on bearings 84 and 85. A carriage 82 is screwed onto the drive shaft 80 and travels vertically following the rotation of the drive shaft 80. A pulley 89 is attached to one end of the drive shaft 80. The second drive source 86 herein is a stepping motor, to which a pulley 88 is fixed. A belt 90 around the pulleys 88 and 89 accordingly transmits rotation of the stepping motor 86 to the drive shaft 80 and in turn the carriage 82. The second holder 74 is joined to the carriage 82 via a link 78 and is guided in its travel by the guide rail 71.

During engagement of the second holder 74 with the first holder 30, current supply to the first stepping motor 43 is lost, wherein rotating the second stepping motor 86 causes the second holder 74 to press on and shift the first holder 30. The external force in so doing compels the first stepping motor 43 to rotate.

In this embodiment, the blood coagulation analyzer is configured such that the first aspirator manipulation unit 10 is shifted back and forth (right and left in FIG. 1) by the third drive source 94, herein also a stepping motor. Moreover, the analyzer is configured such that the first aspirator manipulation unit 10 is shifted laterally (in and out of the plane of FIG. 1) by the fourth drive source 96, also a stepping motor. When the first aspirator manipulation unit 10 is at the front end of the analyzer (right side in FIGS. 1 and 2), the first holder 30 and the second holder 74 come into engagement. When the first aspirator manipulation unit 10 is rearward (left side in the figures), the engagement of the two is released, wherein the pipette 12 is shifted vertically solely by the rotation of the first stepping motor 43.

In this embodiment of the present invention, the sample liquid held in the sample containers is plasma, and the (not shown) sampler sets the sample containers into the sample rack 66, which in this instance can accommodate 10 containers, and conveys them sequentially into position beneath the aspirator. Specifically, the sample rack 66 is shifted intermittently from right to left in the FIG. 6 orientation one container at a time.

The sample containers used in this embodiment are gross divided into three categories. The first type, capped containers A, B, C, D, E, and F, rides on the bottom wall of the sample rack 66 (the container bottoms contact the sample rack bottom wall). The caps on each container differ. The second type, open container G, also rides on the bottom wall of the sample rack 66 (the container bottom contacts the sample rack bottom wall). The third type, open containers H, I, and J, are loaded above the sample rack bottom wall—the containers are either furnished with a flange which sits on the upper wall of the sample rack (H, J), or which sits the upper end of an open container for loading (I). The bottom of any of the third type of open container does not contact the bottom wall of the sample rack.

Figure 6:
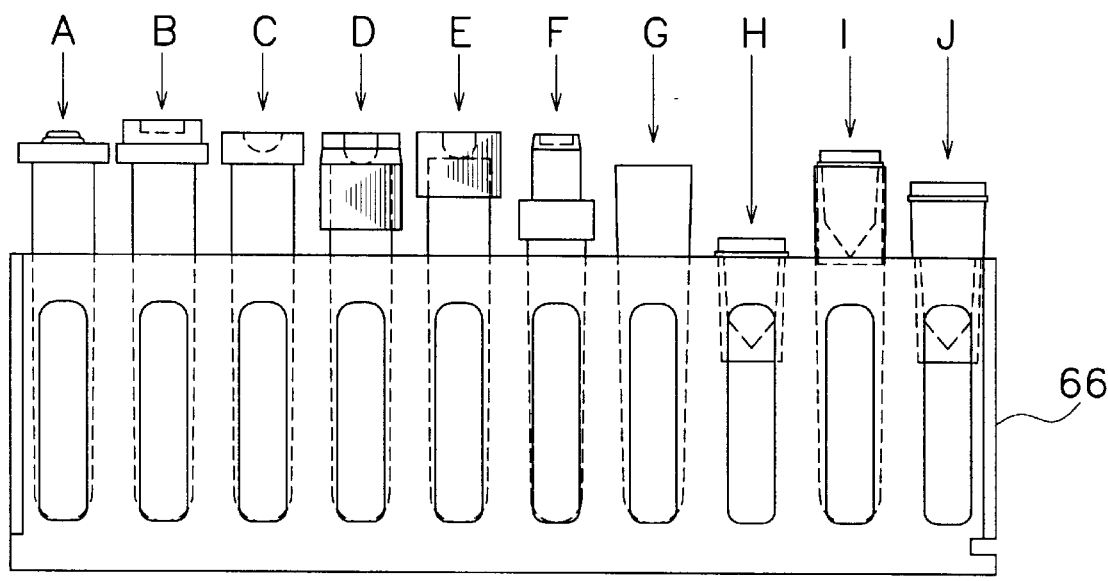
FIG. 6 is a front elevational view of a blood coagulation analyzer sample rack into which a row of vessels is loaded, from which aliquots are taken up by the aspirator.

In the present embodiment, the underside of the through-hole 63 through the washing element 60 flares into a tapered cup 61, enabling containers to be held without slipping out of position even wherein they are peculiar, like container F (vacuum blood-sampling tube "MONOVETTE" made by Sarstedt Co.) in FIG. 6.

Figure 7A:
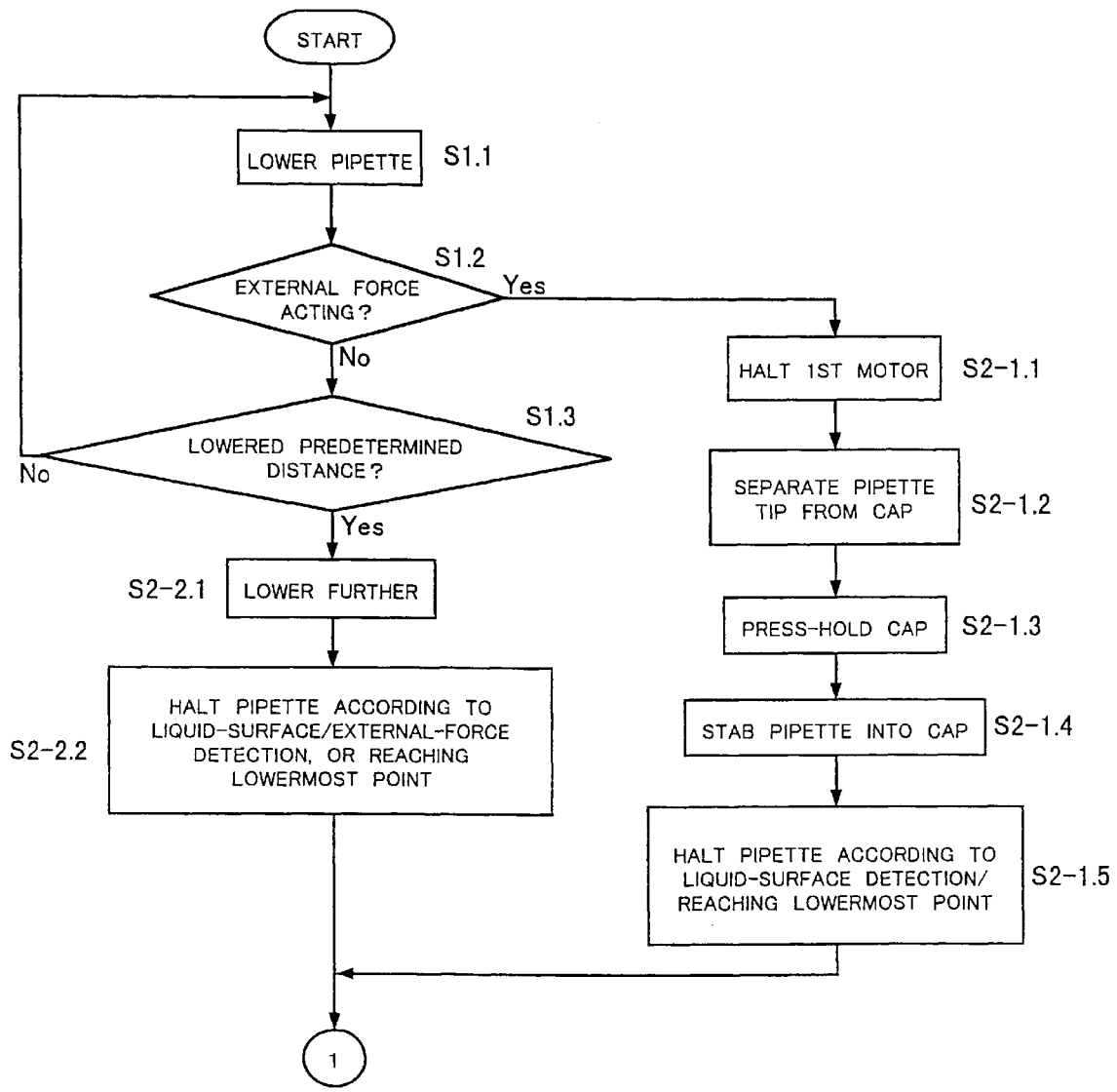
FIGS. 7A and 7B are a flow chart of a control program executed by an aspirator controller in accordance with the present invention.
Figure 7B:
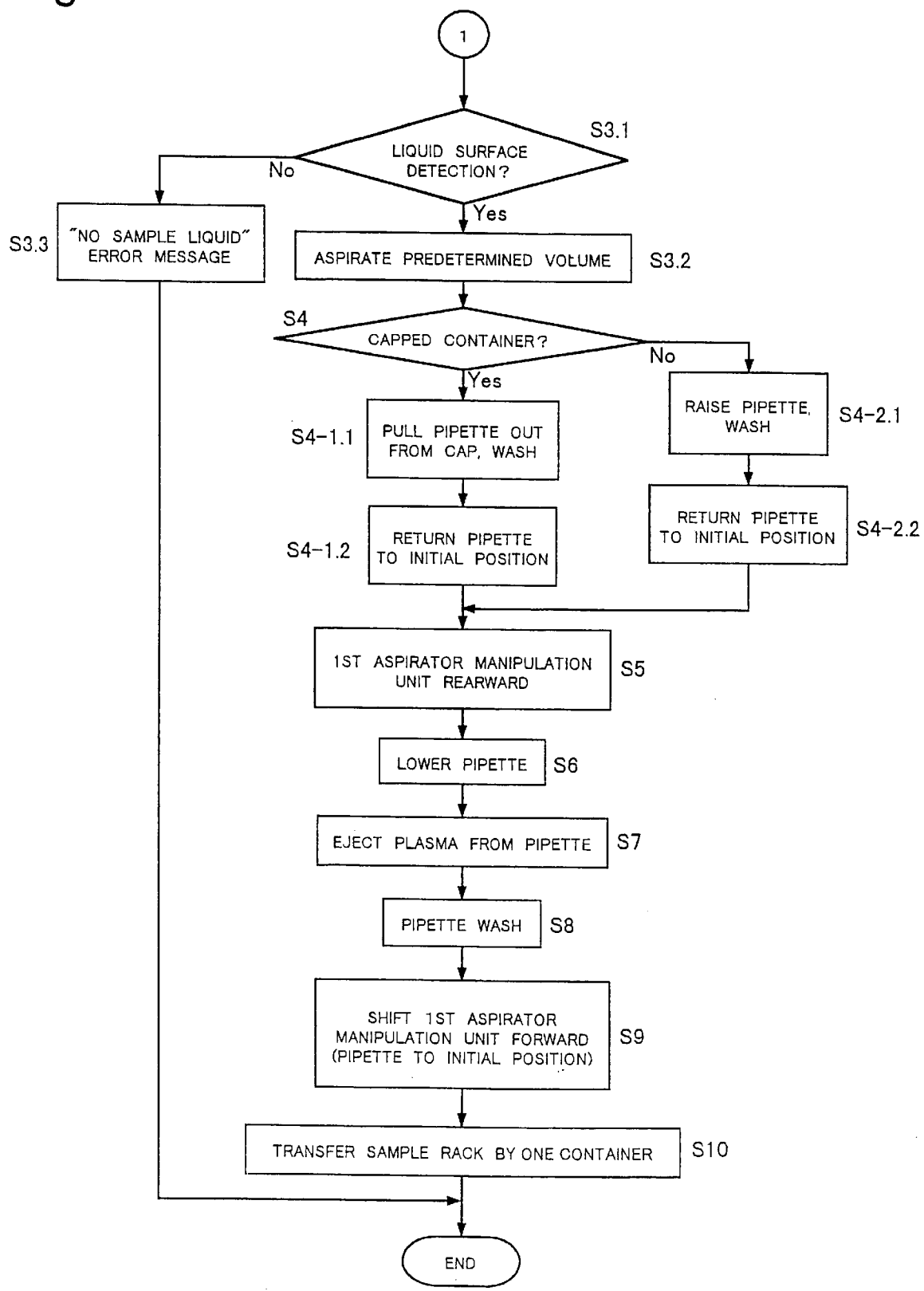

Referring now to the FIG. 7 flow chart, the following details a program for operating the aspirator embodied in a sample analyzer in conformity with the present invention. A control unit 92, indicated in FIG. 1, receives signals from the sensor 53 via the external force detection means 54 and drives each of the stepping motors—i.e., the first through fourth drive sources 43, 86, 94 and 96—respectively in accordance with the program.

Steps S1.1 through S1.3: Detecting Presence of Container Caps

In the situation wherein the first aspirator manipulation unit 10 is located in its forward-most position, the pipette 12 is lowered a predetermined distance from its initial position (uppermost point), going through the washing element 60 (S1.1). The pipette 12 is lowered herein by rotating the first and second stepping motors 43 and 86 to lower together the first and second holders 30 and 74 while maintaining their non-interfering engaged state, as described above. During this operation, in step S1.2 the control unit 92 monitors signals from the external force detection circuit 55. If external force acting on the pipette 12 is detected, the control unit 92 determines that a cap is present on a shut container and, in step S2-1.1, halts the first stepping motor 43. If the control unit 92 does not detect external force acting on the pipette 12 when it has been lowered the predetermined distance, the control unit 92 determines that an open container is present without a cap (S1.3). The capped/uncapped information determined in step S1.2 is stored for reference in step 4, noted below.

Steps S2-1.1 through S2-1.5: Lowering Pipette wherein Container is Capped (Piercing)

Following step S2-1.1, which halts the first stepping motor 43 upon detection of external force in step S1.2, in step S2-1.2 the tip of the pipette 12 is separated from the cap by rotating the halted first stepping motor 43 very slightly in the reverse direction. Then, in step S2-1.3, by running the drive source 72, the tapered cup 61 on the underside of the washing element 60 is lowered onto the cap 69 (as indicated in FIGS. 1 and 2) of the present one of the containers 68 to press-hold it. In step S2-1.4 the current supply to the first stepping motor 43 is stopped and the second stepping motor 86 is rotated, actuating the second holder 74 to push the first holder 30 down, stabbing the pipette 12 through the cap 69 on the present container 68. Herein, accordingly, the power of the second motor 86 alone lowers the pipette 12. Then, in accordance with either liquid-surface detection information from the liquid-surface detection circuit 35, or previously established position information indicating that the pipette 12 has reached a lowermost point, in step S2-1.5 the second stepping motor 86 is halted, which also stops the pipette 12.

Steps S2-2.1 and S2-2.2: Lowering Pipette wherein Container is Open

If the pipette 12 has not encountered an external force acting upon it after it has been lowered the predetermined distance in step S1.3, in step S2-2.1 the pipette 12 is lowered further. Herein, by continuously rotating the first and second stepping motors 43 and 86, the first holder 30 is lowered without it contacting the second holder 74. Accordingly, the power of the first stepping motor 43 lowers the pipette 12. Then, in accordance with information from either the liquid-surface detection circuit 35 or the external force detection circuit 55, or in accordance with previously established position information indicating that the pipette 12 has reached a lowermost point, in step S2-2.2 the first stepping motor 43 is halted, which also stops the pipette 12.

Steps S3.1 Through S3.3: Aspirating Sample Liquid

Step 3.1 determines based on the result of either step S2-2.2 or S2-1.5 whether upon lowering the pipette 12 into the present one of the containers 68 the surface of the liquid sample (plasma) has been detected. If so, in step S3.2, the pipette 12 is lowered a predetermined distance according to the aspiration volume, and the liquid quantity meter 37 is operated to aspirate the predetermined volume (in the present embodiment, 5 to 500 $\mu$l) of plasma through the aperture 18 at the tip of the pipette 12.

If the lowering pipette 12 is halted in step S2-1.5 by reaching its lowermost point, or is halted in step 2-2.2 by the detection of external force or by reaching its lowermost point, that means there is no plasma to be aspirated. Therefore, in step 3.3 a "Will Not Execute Aspiration/No Sample Liquid" error message is output.

Steps S4, S4-1.2 and S41.2: Raising Pipette wherein Container is Capped

If step 4 determines from the information recorded in step S1.2 that the present container 68 is capped, then in step S4-1.1, with the current supply to the first stepping motor 43 stopped, the second stepping motor 86 is reverse-rotated. Accordingly, the second holder 74 pushes up the first holder 30, and the pipette 12 is pulled out of the cap 69 on the present container 68. Herein, the power of the second stepping motor 86 alone raises the pipette 12. At the same time, washing liquid is supplied to the washing element 60 to clean the outer wall of the pipette 12 and waste fluid is discharged. When the pipette 12 is completely pulled out, in step S4-1.2 the washing element 60 is raised to release the hold on the present container 68, and the pipette 12 is returned to the initial position.

Steps S4, S4-2.1 and S4-2.2: Raising Pipette wherein Container is Open

If step 4 determines from the information recorded in step S1.2 that the present container 68 is not capped, then in step S4-2.1 the first and second stepping motors 43 and 86 are reverse-rotated to raise the first holder 30 without it contacting the second holder 74. Herein, solely the power of the first stepping motor 43 raises the pipette 12. At the same time, washing liquid is supplied to the washing element 60 to clean the outer wall of the pipette 12 and waste fluid is discharged. In step S4-2.2 the pipette 12 is returned to the initial position.

Step S5: Shifting Pipette Rearward

Rotating the motor 94 shifts the first aspirator manipulation unit 10 rearward. This accordingly releases the engagement of the first holder 30 with the second holder 74 completely. The first aspirator manipulation unit 10 further may be shifted laterally as necessary by rotating the stepping motor 96.

Step S6: Lowering Pipette

The pipette 12 is lowered a predetermined amount by rotating the first stepping motor 43 only, since engagement of the first holder 30 with the second holder 74 is released.

Step S7: Sample Liquid Ejection

By operating the liquid quantity meter 37, a predetermined volume of plasma is ejected through the aperture 18 in the tip of the pipette 12 into a reaction vessel (not illustrated).

Step S8: Raising Pipette

This step reverse-rotates the first stepping motor 43 to raise the pipette 12. Then, the inner and outer walls of the pipette 12 are cleansed by, for example, driving stepping motor 94 or 96 to transfer the pipette 12 to a not-shown washing vessel, and cleansing it there. Alternatively, the inner and outer walls of the pipette 12 may be cleansed by supplying washing liquid through the inner passage 14, and also supplying washing liquid to the washing element 60, and discharging the waste fluid from the washing element 60.

Step S9: Shifting Pipette Forward

This step reverse-rotates the motor 94 to shift the first aspirator manipulation unit 10 forward, and returns the pipette 12 to its initial position. This brings the first holder 30 into the state in which it can engage with the second holder 74.

Step S10: Sample Rack Transfer

The sampler is driven to shift the sample rack 66 by one container 68, and stopped. Then, the above-noted steps are executed in sequence.

Various details of the present invention may be changed without departing from its spirit nor its scope. Furthermore, the foregoing description of the embodiments according to the present invention are provided for illustration only, and not for the purpose of limiting the invention as defined by the appended claims and their equivalents.

What is claimed is:

1. An aspirator for aspirating from containers disposed at a predetermined position, the aspirator comprising;

a pipette for drawing up liquids, said pipette having a sharply formed tip;

a differential drive-mode driving mechanism for shifting said pipette;

external force detection means for detecting external force acting on said pipette;

a container holder for holding a container in the predetermined position while said pipette is being shifted by said driving mechanism; and control means responsive to said external force detection means for controlling said driving mechanism to shift said pipette towards said container, said control means being configured to determine that the container is not a closed container if an external force is not detected by the external force detection means, and to determine that the container is a closed container if an external force is detected by the external force detection means, wherein the control means based on the determination whether the container is closed directs change in drive mode of said driving mechanism.

2. The aspirator in accordance with claim 1, wherein the control means directs change in operation of said pipette based on the determination whether the container is closed.

3. The aspirator in accordance with claim 1, wherein the driving mechanism comprises:

a first holder for holding and shifting said aspirating tube in its axial direction;

a first drive source for providing shifting force to said first holder;

a second holder for engaging with said first holder to push and shift said first holder in the axial direction of said aspirating tube; and a second drive source for providing shifting force to said second holder; wherein if said control means determines that the container is not a closed container, said control means shifts said first holder without engagement with said second holder using the force of said first drive source, and if said control means determines that the container is a closed container, said control means engages and shifts said first holder with said second holder using the force of said second drive source.

4. The aspirator in accordance with claim 3, further comprising:

liquid-surface detection means for detecting whether the tip of said pipette reaches a liquid surface; wherein if said control means determines that the container is not a closed container, said control means stops said first drive source based on liquid-surface detection information from said liquid-surface detection means or external force detection information from said external force detection means, and if said control means determines that the container is a closed container, said control means stops said second drive source based on liquid-surface detection information from said liquid-surface detection means.

5. The aspirator in accordance with claim 1, wherein the sharply formed tip of said pipette is an obliquely cut surface formed so as not to give rise to any acute-angle edge an the inner circumferential rim of said aspirating tube in the obliquely cut surface.

6. The aspirator in accordance with claim 5, wherein acute-angle edges are removed on at least half of the inner circumferential rim of said pipette.

7. The aspirator in accordance with claim 1, wherein said container holder is a pipette washing element having a through-hole for said pipette, the through-hole flaring in a concavity facing the tip of said pipette.

8. The aspirator in accordance with claim 1, said differential drive-mode driving mechanism comprising drive-force adding means for shifting said aspirating tube with at least two different drive forces; wherein
    the control means directs said drive mechanism to shift said pipette towards said container at a first drive force if the external force is not detected by the external force detection means, and directs said drive-force adding means to shift said pipette at a second drive force greater than the first drive force if the external force is detected by the external force detection means.

9. The aspirator in accordance with claim 1, wherein said differential drive-mode driving mechanism shifts said pipette vertically.

10. An aspirator for aspirating liquid aliquots from a row of capped and uncapped containers horizontally transferred incrementally into an aspiration position in an automated analyzer, the aspirator comprising:
    a needle pipette having an obliquely cut aspiration tip;
    a first aspirator manipulation unit including a first holder for vertically retaining said needle pipette, and a first drive means for vertically translating said first holder into and out of a container in the aspiration position;
    a second aspirator manipulation unit including a second holder configured to enclose said first holder, and a second drive means cooperative with said first drive means for vertically translating said second holder in tandem with said first holder, and operative independently of said first drive means for driving said second holder against said first holder;
    external force sensing means associated with said first aspirator manipulation unit for detecting external force acting on said needle pipette;
    liquid-surface detecting means operative through said needle pipette;
    a controller connected to said first and second drive means and responsive to said external force sensing means and said liquid-surface detecting means, for controlling said first and second aspirator manipulation units; wherein said controller is programmed to
        actuate said first and second drive means to translate vertically said first and second holders in tandem until said needle pipette contacts liquid in a container in the aspiration position if no external force acting on said needle pipette is detected by said external force sensing means;
        halt said first and second drive means if said needle pipette does not contact liquid in the container in the aspiration position after said first and second holders have been translated a predetermined distance; and
        halt said first drive means and continue actuating said second drive means if external force acting on said needle pipette is detected by said external force sensing means.

11. An aspirator as set forth in claim 10, further comprising:
    a washer pierced by a hole penetrable by said needle pipette and opening in a container-cap holder conformation; and
    a washer drive means associated with said controller for shifting said washer vertically; wherein
        if external force acting on said needle pipette is detected by said external force sensing means and said controller halts said first drive means, said controller actuates said washer drive means to press the container-cap holder conformation onto the container in the aspiration position before said controller continues actuating said second drive means.

12. An aspirator as set forth in claim 10, wherein the obliquely cut aspiration tip of said needle pipette is inner-rim chamfered.

* * * * *